United States Patent [19]

Verduijn

[11] Patent Number: 5,242,675
[45] Date of Patent: Sep. 7, 1993

[54] ZEOLITE L

[75] Inventor: Johannes P. Verduijn, Spijkenisse, Netherlands

[73] Assignee: Exxon Research & Engineering Company, Linden, N.J.

[21] Appl. No.: 825,408

[22] Filed: Jan. 24, 1992

Related U.S. Application Data

[63] Continuation of Ser. No. 715,011, Jun. 13, 1991, abandoned, which is a continuation of Ser. No. 501,406, Mar. 29, 1990, abandoned, which is a continuation of Ser. No. 481,484, Feb. 16, 1990, abandoned, which is a continuation of Ser. No. 298,336, Jan. 12, 1989, abandoned, which is a continuation of Ser. No. 918,457, Oct. 14, 1986, abandoned.

[30] Foreign Application Priority Data

Oct. 15, 1985 [GB] United Kingdom ............... 8525404

[51] Int. Cl.$^5$ ............................................. C01B 33/34
[52] U.S. Cl. ................................. 423/700; 423/716; 423/DIG. 28
[58] Field of Search ............... 423/328, 329, 330, 700, 423/716, DIG. 28

[56] References Cited

U.S. PATENT DOCUMENTS

| 3,216,789 | 8/1965 | Breck et al. | 423/328 |
|---|---|---|---|
| 3,298,780 | 3/1967 | Fleck | 502/60 |
| 3,794,600 | 1/1972 | Schutt | 502/74 |
| 3,867,512 | 9/1972 | Young | 423/329 |
| 4,104,320 | 8/1976 | Bernard et al. | 423/328 |
| 4,124,491 | 5/1972 | Antos et al. | 208/139 |
| 4,157,989 | 5/1978 | Antos | 252/441 |
| 4,165,276 | 9/1977 | Antos | 208/139 |
| 4,206,040 | 10/1978 | Antos | 208/139 |
| 4,231,897 | 5/1979 | Antos | 252/441 |
| 4,295,959 | 10/1980 | Antos | 208/138 |
| 4,295,960 | 11/1980 | Antos | 208/139 |
| 4,544,539 | 10/1985 | Wortel | 423/328 |
| 4,894,214 | 1/1990 | Verduijn et al. | 423/329 |

FOREIGN PATENT DOCUMENTS

| 0888365 | 10/1985 | Belgium . |
|---|---|---|
| 0040119 | 4/1981 | European Pat. Off. . |
| 0096479 | 5/1983 | European Pat. Off. . |
| 0142347 | 9/1984 | European Pat. Off. . |
| 0142348 | 9/1984 | European Pat. Off. . |
| 0142349 | 9/1984 | European Pat. Off. . |
| 0142351 | 9/1984 | European Pat. Off. . |
| 0142352 | 9/1984 | European Pat. Off. . |
| 0142353 | 9/1984 | European Pat. Off. . |
| 0142354 | 9/1984 | European Pat. Off. . |
| 0142355 | 9/1984 | European Pat. Off. . |
| 0145289 | 9/1984 | European Pat. Off. . |
| 0088789 | 7/1970 | German Democratic Rep. . |
| 1202511 | 1/1969 | United Kingdom . |
| 1393365 | 9/1971 | United Kingdom . |
| 2114150 | 1/1983 | United Kingdom . |
| 2116450 | 1/1983 | United Kingdom . |
| 2142648 | 6/1984 | United Kingdom . |

OTHER PUBLICATIONS

Comptes Rendus Acad. Sci. Ser. C 275 #21: 1215–1217 (1972), Frety et al.
Nippon Kagaku Zasshi 91, pp. 1046–1049, Nishimura, Nov. 1970.
Doklady Akademii Nauk SSSR, V. 243, No. 2, pp. 438–440, Tsitsishvili et al. 1978.
Chemical Abstracts vol. 90, 573478, L. Wilkosz, 1979.

Primary Examiner—R. Bruce Breneman

[57] ABSTRACT

Zeolite L with flat basal planes, and reduced crystallite size is prepared in a synthesis modified by the addition of small amounts of additional metal such as magnesium, calcium, barium, cobalt, zinc, chromium, manganese or nickel. The addition of these metals also suppresses unwanted zeolite W formation even when the synthesis would otherwise form this zeolite.

28 Claims, No Drawings

ZEOLITE L

This application is a continuation of U.S. Ser. No. 07/715,011, filed Jun. 13, 1991, now abandoned, which is a continuation of U.S. Ser. No. 07/501,406, filed Mar. 29, 1990, now abandoned, which is a continuation of U.S. Ser. No. 07/481,484, filed Feb. 16, 1990, now abandoned, which is a continuation of U.S. Ser. No. 07/298,336, filed Jan. 17, 1989, now abandoned, which is a continuation of U.S. Ser. No. 06/918,457, filed Oct. 14, 1986, now abandoned.

This invention relates to a highly crystalline zeolite L, its preparation and use in catalysts, particularly for aromatization. In particular, it relates to zeolite L with cylindrical morphology, which provides a catalyst base giving extended lifetimes in the dehydrocyclization of alkanes.

Zeolite L has been known for some time as an adsorbent, and in U.S. Pat. No. 3,216,789 is described as an aluminosilicate of the formula:

$$0.9-1.3M_{2/n}O:Al_2O_3:5.2-6.9SiO_2:yH_2O$$

(where M is an exchangeable cation of valence n and y is from 0 to 9) having an x-ray diffraction pattern with the following more significant d(Å) values:

| |
|---|
| 16.1 ± 0.3 |
| 7.52 ± 0.04 |
| 6.00 ± 0.04 |
| 4.57 ± 0.04 |
| 4.35 ± 0.04 |
| 3.91 ± 0.02 |
| 3.47 ± 0.02 |
| 3.28 ± 0.02 |
| 3.17 ± 0.01 |
| 3.07 ± 0.01 |
| 2.91 ± 0.01 |
| 2.65 ± 0.01 |
| 2.46 ± 0.01 |
| 2.42 ± 0.01 |
| 2.19 ± 0.01 |

The preparation of zeolite L described in U.S. Pat. No. 3,216,789 comprises crystallizing the zeolite from a reaction mixture comprising mole ratios:

| | |
|---|---|
| $K_2O/(K_2O + Na_2O)$ | 0.33–1 |
| $(K_2O + Na_2O)/SiO_2$ | 0.35–0.5 |
| $SiO_2/Al_2O_3$ | 10–28 |
| $H_2O/(K_2O + Na_2O)$ | 15–41 |

The silica to alumina ratio in this reaction mixture is significantly higher than the ratio in the formed zeolite.

British Patent 1,202,511 describes a revised zeolite L preparation using lower proportions of silica in the reaction mixture which comprises mole ratio of reactants as:

| | |
|---|---|
| $K_2O/(K_2O + Na_2O)$ | 0.7–1 |
| $(K_2O + Na_2O)/SiO_2$ | 0.23–0.35 |
| $SiO_2/Al_2O_3$ | 6.7–9.5 |
| $H_2O/(K_2O + Na_2O)$ | 10.5–50 |

The ratio $H_2O/(K_2O+Na_2O+SiO_2+Al_2O_3)$ is preferably not greater than 6 to give a "dry gel".

U.S. Pat. No. 3,867,512 discloses a preparation of zeolite L from a reaction mixture having a molar composition:

| | |
|---|---|
| $K_2O/(K_2O + Na_2O)$ | 0.3–1 |
| $(K_2O + Na_2O)/SiO_2$ | 0.3–0.6 |
| $SiO_2/Al_2O_3$ | 10–40 |
| $H_2O/(K_2O + Na_2O)$ | 45–140 | in which the silica source is a gel having at least 4.5 weight percent water and prepared in a particular manner.

L. Wilkosz in Pr Chem 409 (1974)—Chemical Abstracts, Vol. 90 (1979) 573478 describes the preparation of zeolite L from a synthesis sol prepared by treating a solution containing silica, potassium hydroxide and sodium hydroxide with a second solution containing potassium aluminate, potassium hydroxide and sodium hydroxide and crystallizing for 72 hours at 20° C. and 122 hours at 100° C. The zeolite L product has a $SiO_2$:$Al_2O_3$ ratio of 6.4:1.

G. V. Tsitsishvilli et al in Doklady Akademii NaukSSSR, Vol. 243, No. 2, pp 438–440 (1978) describe the synthesis of zeolite L from alumina-silica gels containing tributylamine. The gels used had the following molar ratios:

| | |
|---|---|
| $SiO_2$:$Al_2O_3$ | 25 |
| $(K_2O + Na_2O)$:$Al_2O_3$ | 18 |
| $(K_2O + Na_2O)$:$SiO_2$ | 0.72 |
| $H_2O/K_2O + Na_2O$ | 20 |
| $K_2O$:$Na_2O$ | 0.5 |

Y. Nishiimura in Nippon Kagaku Zasshi 91, 11, 1970, pp 1046-9 describes in general terms zeolite L preparation from a synthesis mixture containing colloidal silica, potassium aluminate and potassium hydroxide having a $SiO_2$:$Al_2O_3$ ratio of 15–25, but exemplifies only two synthesis mixtures having the following ratios of components:

$$7K_2O:Al_2O_3:20SiO_2:450H_2O$$

and $$8K_2O:Al_2O_3:10SiO_2:500H_2O$$

Frety et al in C.R. Acad Sc. Paris, t275, Serie c-1215 describes the electron microscopy examination of zeolite L in which particles were said to be observed in the form of slightly deformed cylinders with very variable dimensions.

U.S. Pat. No. 3,298,780 describes a related zeolite known as UJ prepared from an aqueous reactant solution having a composition, expressed as molar ratios of oxides, corresponding to:

$SiO_2/Al_2O_3$ of from 6 to 30

$R_{2/u}O/SiO_2$ of from 0.30 to 0.70, and $H_2O/R_{2/u}O$ of from 80 to 140 at a temperature between 150° F. (65.6° C.) and 325° F. (162.8° C.) until the zeolite crystals are formed.

Zeolite UJ is described as having nearly cubic shaped crystals with a crystal size ranging upward from 0.05 micron.

GB 1,393,365 describes a further related zeolite known as AG1 which is prepared by reacting at least one aluminium component, at least one silicon component and at least one alkali metal component, in an aqueous medium, the sole or major silicon component being a water glass having a molar ratio $SiO_2/M_2O$ of 3.5 to 4.0 to give a reaction mixture with oxide molar ratios in one of the following ranges:

| Range 1 | |
|---|---|
| $SiO_2/Al_2O_3$ | 7–14 |
| $(K_2O + Na_2O)/SiO_2$ | 0.25–0.85 |
| $K_2O/(K_2O + Na_2O)$ | 0.75–1 |
| $H_2O/(K_2O + Na_2O)$ | 25–160 |
| Range 2 | |
| $SiO_2/Al_2O_3$ | 14–20 |
| $(K_2O + Na_2O)/SiO_2$ | 0.25–0.85 |
| $K_2O/(K_2O + Na_2O)$ | 0.5–1 |
| $H_2O/(K_2O + Na_2O)$ | 25–160 |
| Range 3 | |
| $SiO_2/Al_2O_3$ | 20–40 |
| $(K_2O + Na_2O)/SiO_2$ | 0.25–1 |
| $K_2O/(K_2O + Na_2O)$ | 0.4–1 |
| $H_2O/(K_2O + Na_2O)$ | 25–160 |

EP0096479 describes zeolite L crystallites in the form of distinct circular cylinders with a mean diameter of at least 0.5 micron and an aspect ratio of at least 0.5, and their preparation in which an alkaline reaction mixture comprising water, a source of silicon and a source of aluminium with a composition falling within the following molar ratios (expressed as oxides):

| $M_{2/n}O/SiO_2$ | 0.22–0.36 |
|---|---|
| $H_2O/M_2O$ | 25–90 |
| $SiO_2/Al_2O_3$ | 6–15 |

(wherein M is a cation of valence n, and preferably potassium or a mixture of $K+M^1$ in which $M^1$ is an alkali metal or alkaline earth metal such as sodium, calcium, barium, or rubidium, provided that $K_{2/n}O/(M^1_2O+K_2O)$ is at least 0.7) is heated to a temperature of from at least 75° C. and preferably from 100° C. to 250° C., more preferably from 120° C. to 225° C., to form the desired cylindrical aluminosilicate.

EP0142353 describes a process for the preparation of zeolite L in which an alkaline reaction mixture comprising water, a source of silicon and a source of aluminium with a composition having the following molar ratio (expressed as oxides):

| $M_{2/n}O/SiO_2$ | 0.22–0.30 |
|---|---|
| $H_2O/M_2O$ | 25–45 |
| $SiO_2/Al_2O_3$ | 10–12 |

(wherein M is as defined hereinbefore) is heated to a temperature of greater than 150° C. for a period long enough to form zeolite L.

EP0142354 describes a process for the preparation of zeolite L in which an alkaline reaction mixture comprising water, a source of silicon and a source of aluminium with a composition having the following molar 5 ratio (expressed in oxides):

| $M_{2/n}O/SiO_2$ | 0.24–0.35 |
|---|---|
| $H_2O/M_2O$ | 35–80 |
| $SiO_2/Al_2O_3$ | 5.7–7.8 |

(wherein M is as defined hereinbefore) is heated to a temperature of greater than 200° C. to form zeolite L.

Further zeolite L preparations are described in EP0142355, EP0142347, EP0142348 and EP0142349.

It was subsequently found that zeolite L may be used as a catalyst base in aromatization reactions. U.S. Pat. No. 4,104,320 disclosed dehydrocyclization of aliphatic compounds in the presence of hydrogen using a catalyst comprising zeolite L and a group VIII metal, in which the zeolite L is of the formula:

$$M_{9/n}(AlO_2)_9(SiO_2)_{27}$$

(where M is a cation of valence n) but the silica to alumina ratio may vary from 5 to 7. Zeolite L is described as occuring in the form of cylindrical crystals a few hundred Angstroms in diameter.

East German Patent 88789 discloses dehydrocyclization using a catalyst formed from a zeolite precursor with a silica to alumina ratio of up to 70. Zeolite L is mentioned as a precursor.

European Patent Application Publication 40119 discloses a dehydrocyclization process operating at low pressure (1 to 7 bars) or low $H_2$/hydrocarbon ratio using a catalyst comprising platinum on a potassium zeolite L. BE 888365 describes dehydrocyclization using a catalyst comprising platinum, rhenium (incorporated in the form of its carbonyl) and sulphur to give an atomic ratio of sulphur to platinum of 0.05 to 0.6 on a zeolitic crystalline aluminosilicate base such as zeolite L. BE792608 discloses the treatment of zeolite L for use as catalyst in isomerization by exchange with ammonium and chromium ions. EP0142351 describes a method for improving the dispersion of noble metal particles on zeolite L to provide an improved reforming catalyst. EP0145289 describes a catalyst comprising zeolite L and highly dispersed particles of a Group VIII metal.

GB2116450 describes a zeolite catalyst comprising a zeolite of the L family, at least one Group VIII metal and an alkaline earth metal selected from barium, strontium and calcium. The catalyst is used for reforming, dehydrocyclizing acyclic hydrocarbons, dehydroisomerizing alkylcyclopentanes and dealkylating toluene. Process using such catalyst are described in GB2114150 and GB2142648.

It has now been found that an improved zeolite L, but having a characteristic morphology and/or size and/or cation content and/or silica/alumina ratio is particularly valuable for use as a catalyst base in hydrocarbon conversions such as aromatization.

The prior art, and particularly EP 0096479, EP 0142353 and EP 0142354, teaches that in zeolite L synthesis a reduction in alkalinity leads to zeolite W formation, and also to larger crystallites. It has surprisingly now been found that by incorporation of certain additional metals in the synthesis gel zeolite L may be made at low alkalinities and under conditions which normally favour formation of other zeolite species. Furthermore small crystallites may be obtained with a particular shape which has shown advantages in catalyst performance.

Thus, in one aspect this invention concerns zeolite L comprising crystallites in the form of cylinders with basal planes of such a shape that the ratio of axial length of curved cylindrical surface (m) to the overall axial length of the crystallite (h) is greater than 0.9, and preferably approaches 1. A geometrically perfect cylinder with completely flat basal planes would have m=h, and m/h=1, while any doming or growths on the basal surfaces mean that h is greater than m, and m/h is less than 1. We have now found that more perfect cylinders, with flatter basal planes than obtained in EP0096479, result in a zeolite L product with better catalytic performance.

The cylindrical crystallites preferably have a mean diameter (d) of at least 0.05μ, more preferably at least 0.1μ. The aspect ratio (the ratio of the axial length of the cylindrical surface m to the mean diameter d) is preferably at least 0.5, more preferably at least 0.75 and most preferably at least 1.

A particularly preferred zeolite L of the invention comprises crystallites in the form of well-defined, smooth-surfaced cylinders with substantially flat basal planes, and thus a m/h ratio of substantially unity, a mean diameter d of from 0.1 to 0.5μ, and an aspect ratio of (m/d) from 0.75 to 5.

Preferably the zeolite L comprises cylindrical crystallites wherein at least 80%, more preferably at least 90%, of the basal planes are microscopically flat to within 200 Å, and thus do not exhibit spiral step growths thereon.

The zeolite L of the invention may also have a relatively high silica/alumina ratio. The cylindrical crystallites described in EP0096479 have silica/alumina ratio of not greater than 6.3, and zeolite L products described therein with higher silica/alumina ratio were in the form of clams or discs (that is, with an aspect ratio of less than 0.5). Thus, a preferred aspect of the invention comprises zeolite L in the form of cylindrical crystallites having an aspect ratio of at least 0.5 and a silica/alumina ratio of greater than 6.5.

The zeolite L of the invention is characterised by its cylindrical morphology. The terms "cylinder" and "cylindrical" are used herein to describe the shape of a cylinder as defined in solid geometry—that is, a solid bounded by a surface generated by a line moving parallel to a fixed line so as to cut a fixed plane curve and by two parallel planes (bases) which cut the surface. The cylinders will generally be circular cylinders, that is, with circular cross-section, but in the context of the invention the cylinders may also exhibit some flattening of the cylindrical surface such that the cross-section has polygonal, and particularly hexagonal character—that is to say, is in the form of a curvilinear hexagon—and the terms "cylinder" and "cylindrical" are used to include such forms.

The zeolite L of the invention displays an x-ray diffraction pattern typical for zeolite L, subject to the changes in position and intensity of the x-ray lines discussed in EP0096479. Occasionally, additional lines not belonging to the pattern for zeolite L appear in a pattern along with the x-ray lines characteristic of the zeolite. This is an indication that one or more additional crystalline materials are mixed with zeolite L in the sample being tested. It is a preferred feature of the invention that the amount of such additional crystalline materials is minimised in the zeolite material as synthesized. In particular, it is preferred that the synthesis of the zeolite of the invention is conducted so that the amount of zeolite W in the product of the synthesis is minimised. Further, the synthesis of the zeolite of the invention is preferably conducted such that the product of the synthesis is substantially free of any additional crystalline phase giving rise to a line in the x-ray pattern at d (Å) value of 6.28±0.05.

The zeolites of the invention are preferably aluminosilicates and will be described hereinafter in terms of aluminosilicates, though other elemental substitutions are possible, for example aluminium may be substituted by gallium, boron, iron and similar trivalent elements, and silicon may be substituted by elements such as germanium or phosphorus. The aluminosilicates preferably have a composition (expressed in terms of molar ratios of the constituent oxides in anhydrous form) of:

$(0.9-1.3)M_{2/n}O:Al_2O_3:xSiO_2$ wherein M represents one or more cations of valence n, x is from 5 to 7.5, preferably from 6.5 to 7.5. The zeolite materials of the invention have high crystallinity as shown by a well-defined x-ray diffraction pattern (without binder or other diluents present) with sharp peaks.

The exchangeable cation M in general formula I is potassium, but it is possible for a part of M to be replaced by other cations such as alkali metals for example sodium. As described hereinafter, such cations may be introduced during synthesis. The ratio $M_{2/n}O:Al_2O_3$ is preferably from 0.95 to 1.15 and generally above 1.

The aluminosilicate forms of the invention may be hydrated, typically with from 0 to 9 moles of water per mole of $Al_2O_3$. When used as a catalyst base, as described hereinafter, the zeolite of the invention is preferably first calcined to remove water. In normal preparation from aqueous gels a hydrated form is first prepared and this may be dehydrated by heating.

Cylindrical particles have been shown in EP0096479 to have excellent properties of extending catalyst life when used as catlyst bases for aromatization catalysts as compared to the morphologies produced by prior art processes. It is now found that particles of this invention provide a means of extending catalyst life still further and/or giving surprising increases in activity in aromatization and/or in selectivity to aromatic products and-/or show increased stability.

It is further surprising feature of the invention that the improved zeolite L with cylindrical morphology may be prepared in the presence of small amounts of additional metals, preferably alkaline earth metals and certain transition metals by controlling the composition of the reaction mixture within certain limits, which in the absence of additional metal do not necessarily result in the desired zeolite L.

In another aspect, therefore, the invention provides a process for the preparation of zeolite L crystallites in the form of cylinders, in which an alkaline reaction mixture comprising water, a source of an alkali metal, a source of silicon, a source of aluminium and a source of an additional metal $M^{11}$, with a composition falling within the following molar ratios (expressed as oxides):

| | |
|---|---|
| $(M^1_2O + M^{11}_{2/n}O)/SiO_2$ | 0.18–0.36 |
| $H_2O/(M^1_2O + M^{11}_{2/n}O)$ | 25–90 |
| $SiO_2/Al_2O_3$ | 5–15 |
| $M^1_2O/M^1_2O + M^{11}_{2/n}O)$ | 0.9–0.9999 |

(wherein $M^1$ is an alkali metal, $M^{11}$ is magnesium, calcium, barium, manganese, chromium, cobalt, nickel or zinc cation and n is the valence of $M^{11}$) is heated to a temperature of from at least 75° C. and preferably from 100° C. to 250° C., more preferably from 120° C. to 225° C., to form the zeolite L of the invention.

There are five principal components to the reaction mixture of synthesis gel and thus generally:
aluminium
silicon
alkali metal, preferably potassium
additional metal $M^{11}$
water
and the relative proportions of these components and the chosen reaction conditions are important if the desired zeolite L of the invention is to be obtained.

Zeolite W tends to be formed as a contaminant in zeolite L preparation at some extremes of gel composition. It is advantageous for the zeolite W content of the product to be minimized. The zeolite W content of the product can be monitored by its x-ray diffraction pattern.

A characteristic prominent line 35 in the zeolite W XRD pattern is at $2\theta=12.6°$ ($d=7.09$ Å), while a prominent line in the zeolite L XRD pattern is at $2\theta=22.7°$ ($d=3.91$ Å). The relative peak intensities of these peaks can be compared to determine the relative proportions of the two zeolite types, since these peaks are not obscured in mixtures of the two zeolites. It is a preferred feature that zeolite of the invention has an XRD pattern in which the peak height ratio $(d=7.09$ Å$)/(d=3.91$ Å$)$ is not greater than 0.2. Very preferably the product is substantially free of zeolite W as evidenced by an absence of the XRD pattern of a line at a d spacing of 7.09 Å. As described in EP0096479, it was previously thought necessary to avoid contamination for the reaction mixture to comprise the reactants in the following molar ratios:

$$M_{2/n}O/SiO_2 = >0.25$$

$$B_2O/M_{2/n}O = <65$$

$$SiO_2/Al_2O_3 = 7.5-10.5$$

It is a surprising feature of the present invention that a highly crystalline product of the invention, substantially free of zeolite W may be obtained from a reaction mixture outside the ranges taught by the prior art, and specifically in which:

$$M_{2/n}O/SiO_2 < 0.25 \text{ and/or}$$

$$H_2O/M_{2/n}O > 65 \text{ and/or}$$

$$SiO_2/Al_2O_3 = 5-7.5$$

by selecting a reaction mixture such that M is a mixture of $M' + M^{11}$ where:

$$M^1_2O/(M^1_2O + M^{11}_{2/n}O) = 0.900-0.9999$$

Thus, in another aspect this invention provides a process for the preparation of zeolite L, in which a reaction mixture comprising water, a source of alkali metal, a source of silicon, a source of aluminium and a source of an additional metal $M^{11}$ is heated to a temperature of at least 75° C. to form the desired zeolite L, the reaction mixture being such that in the absence of the additional metal $M^{11}$ the formed product would comprise substantial amounts of zeolite W, in which the presence of the additional metal $M^{11}$ results in reduced contamination by zeolite W. It is surprisingly found that very small amounts (even in some systems as low as a few parts per million) of the additional metal are effective at suppressing zeolite W, though the zeolite W level in the product depends upon other components of the reaction mixture.

The effect of the additional metal $M^{11}$ in supressing the tendency to zeolite W formation in a zeolite L reaction gel is extremely valuable since it effectively expands the range of reaction mixtures which can be used to obtain a high quality zeolite L product. The effect of $M^{11}$ in suppressing zeolite W formation may also be demonstrated by using different crystallisation conditions. In general, a zeolite L crystallisation gel is extremely susceptible to zeolite W contamination if subjected to shear forces—for example, by stirring the gel during crystallisation. We have now found that zeolite L may be prepared in a stirred crystallisation by incorporating additional metal $M^{11}$ in the gel. The invention extends to a stirred process for zeolite L formation in which the tendency to zeolite W formation is be prevented by incorporation of a metal $M^{11}$ in the reaction mixture. The reaction mixture may, for example, be a gel as described in EP0096479 to which a zeolite W-suppressing amount of $M^{11}$ is added.

Thus, in a further aspect, this invention provides a method of supressing zeolite W formation in the preparation of zeolite L from a crystallisation gel in which the gel composition and/or crystallisation conditions such as stirring would otherwwise allow zeolite W formation, which method comprises introducing into the gel a zeolite W-suppressing amount of a source of an additional metal $M^{11}$. The zeolite W-suppressing amount is as indicated above surprisingly small, and since the additional metal also tends to result in smaller crystallite size in the product, it will not be desirable to increase the amount of additional metal beyond the level at which zeolite W is suppressed if smaller crystallites are not wanted. It has been found that the best results are obtained at extremely low, but non-zero, amounts of additional metal.

The alkali metal M' is very preferably potassium (K), but may be a mixture of potassium with other alkali metals, for example sodium. It is a further surprising feature of the invention that a greater degree of replacement of potassium by other alkali metals in possible in the presence of the additional metal without significant amounts of zeolite W being formed in the Zeolite L product. EP0096479 indicates that the preferred maximum amount of alkali metal other than potassium is 30 mole % of the total alkali metal content. We have found that at this level of other alkali metal and even at greater levels the tendency to form zeolite W may be substantially completely suppressed by the presence of the additional metal $M^{11}$.

Thus, the preferred zeolites of the invention may be obtained within the following preferred ranges:

| | |
|---|---|
| $(M^1_2O + M^{11}_{2/n}O)/SiO_2$ | 0.18–0.26 |
| $H_2O/(M^1_2O + M^{11}_{2/n}O)$ | 50–90 |
| $SiO_2/Al_2O_3$ | 6–12 |
| $M^1_2O/(M^1_2O + M^{11}_{2/n}O)$ | 0.959–0.9999 | where $M^1$ is potassium or a mixture of potassium and a second alkali metal $M^2$ and $K_2O/K_2O + M_2O = 0.5-1$.

The amount of the additional metal $M^{11}$ may be very low, only a few ppm of the reaction mixture, and yet still have an effect in promoting zeolite L formation, forming smaller and/or more cylindrical zeolite L particles and/or promoting the properties of the zeolite L product. Thus in a further aspect this invention provides a process of preparing zeolite L in which there is added to the synthesis gel prior to crystallization a source of an additional metal $M^{11}$, in an amount such that the amount of additional metal in the gel is from 0.1 ppm to 0.1 wt % of the gel, preferably from 5 ppm to 0.05 wt % of the gel.

In addition to varying the proportions of the reactants in the reaction mixture, it is possible to vary the reaction conditions and in particular the crystallisation temperature. By using different temperatures, it may be possible to deviate further from the preferred composition defined above and yet still obtain the desired product. In general, within the broad reactant ratios defined for the process of the invention, a higher crystallisation temperature enables the silicon content to be lowered and/or the water content to be lowered and/or the potassium content (and thus the alkalinity) to be raised. By contrast, operating at lower temperatures tends to decrease the nucleation rate which can be countered by lowering the alkalinity and/or by increasing the water content and/or by introducing seeds of preformed zeolite L. Increasing the alumina content enables higher yields of zeolite L to be obtained, whereas the prior art teaches that this leads to zeolite W formation.

The additional metal $M^{11}$ may be introduced as any convenient compound such as an oxide, carbonate, silicate hydroxide or sulphate. Barium sulphate has been found an effective source of barium even though not soluble in the reaction medium. The additional metal $M^{11}$ is preferably magnesium, calcium, barium, zinc or cobalt though chromium manganese or nickel may also be employed.

The function of the additional metal is not wholly understood but at least some of the metals are believed to form highly insoluble silicates which may form very fine suspensions of silicate particles which will function as nuclei or seeds for zeolite L formation. Thus additional metals forming highly insoluble silicates are preferred.

In the synthesis of all zeolitic materials of the invention, the source of silicon for the reaction mixture is generally silica, and this is usually most conveniently in the form of a colloidal suspension of silica such as Ludox HS 40 available from E. I. Dupont de Nemours and Co. Colloidal silica sols are preferred since they result in less contaminating phases. However, other forms such as silicates may be used.

The source of aluminium may be an alumina introduced into the reaction medium as, for example, $Al_2O_3.3H_2O$, previously dissolved in alkali. However, it is also possible to introduce aluminium in the form of the metal, which is dissolved in alkali.

The aluminosilicates of the invention are preferably obtained from reaction mixtures containing potassium. This potassium is preferably introduced as potassium hydroxide.

The product of the processes described above is a mixed cation form of the zeolite containing alkali metal, preferably potassium, and metal $M^{11}$. The molar ratio of $K_2O/(K_2O+M^{11}{}_{2/n}O)$ in the product of the invention is preferably greater than 0.95, more preferably greater than 0.98. The amount of the cation $M^{11}$ in the zeolite is preferably less than 0.1 wt % of the zeolite L, and may be below 0.05 wt % of the zeolite L. By ion exchange of the product in the manner conventional to zeolite chemistry, other cations can be introduced. However it is a surprising feature of the invention that the cation $M^{11}$ cannot be completely replaced by ion exchange indicating that some of them at least of the $M^{11}$ cations are in non-exchangeable sites in the zeolite L structure.

Within the ranges specified hereinbefore for the composition of the reaction mixture, it is possible to choose ratios of oxides and alkalinity to given particular forms of the aluminosilicate product. The $SiO_2/Al_2O_3$ ratio in the reaction mixture may vary over a wide range but the $SiO_2/Al_2O_3$ ratio in the product preferably lies in a relatively narrow range of 5.4 to 7.4. The higher the $SiO_2/Al_2O_3$ ratio in the reaction mixture, the higher the ratio in the product. Also, decreasing alkalinity ($OH^-/SiO_2$) tends to increase the $SiO_2/Al_2O_3$ ratio in the formed product. Dilution of the reaction mixture with water and thus increasing the $H_2O/K_2O$ ratio also tends to increase the $SiO_2/Al_2O_3$ ratio in the product.

Particle size is also affected by the composition of the reaction mixture and the nature of the raw materials used. Generally, the particles formed are in the range of from 0.05 to 4.0$\mu$, but the use of the metal $M^{11}$ tends to favour small particles, despite the low alkalinity of the synthesis gel. However, even in the presence of $M^{11}$ larger, but still small, particle sizes are favoured by lower alkalinity. Higher dilution and high temperatures tend to favour formation of particles with an increased m/d ratio.

Crystallisation time is related to the crystallisation temperature. The crystallisation is preferably carried out in the region of 150° C. and at this temperature the crystallisation time may be from 24 to 96 hours, typically from 48 to 72 hours. Lower temperatures may require much longer times to achieve good yield of the desired product, whereas times of less than 24 hours are possible when higher temperatures are used. A time of 8 to 15 hours is typical for a temperature of 200° C. or greater.

The crystallisation is generally carried out in a sealed autoclave and thus at autogenous pressure. It is generally inconvenient, although possible, to employ higher pressures. Lower pressure will require longer crystallisation times.

Following the preparation as described above the zeolite L may be separated, washed and dried in the normal manner.

The product of the processes of the invention described hereinbefore are preferably substantially free from contaminant crystalline and amorphous materials. However, in employing these products in catalytic applications it may be desired to combine them with additional crystalline or amorphous materials and this invention extends to such combinations.

We have found that the zeolite L of the invention is an excellent catalyst base and may be used in a wide variety of catalytic reactions. The particular morphology of the crystals appears to result in a particular stable base for catalytically active metals with a surprising resistance to metal catalyst deactivation. In addition, the zeolite L of the invention has displayed low acidity which makes it especially suited to catalytic applications where a low acid site strength is advantageous such as aromatisation.

The catalytically-active metal(s) may be, for example, a Group VIII metal such as platinum, tin, or germanium as described in U.S. Pat. No. 4,104,320, or a combination of platinum and rhenium as described in GB 2,004,764 or BE 888365. In the latter case, the catalyst may for appropriate circumstances also incorporate halogen as described in U.S. Pat. No. 4,165,276, silver as described in U.S. Pat. Nos. 4,295,959 and 4,206,040, cadmium as described in U.S. Pat. Nos. 4,295,960 and 4,231,897 or sulphur as described in GB 1,600,927.

We have found a particularly advantageous catalyst composition to incorporate from 0.1 to 6.0 weight %, preferably from 0.1 to 1.5 weight % platinum or palladium, since this gives excellent results in aromatisation. From 0.4 to 1.2 weight % platinum is particularly preferred, especially in conjunction with the potassium form of the aluminosilicate. The invention extends to catalysts comprising the zeolitic material and a catalytically-active metal.

It may also be useful to incorporate into the catalyst of the invention one or more materials substantially inert under the conditions in which the catalyst is to be employed to act as a binder. Such binders may also act to improve the resistance of the catalyst to temperature, pressure and attrition.

The zeolite L of the invention may be used in a process for the conversion of a hydrocarbon feed in which the feed is contacted with a catalyst as described above under appropriate conditions to bring about the desired conversion. They may, for example, be useful in reactions involving aromatisation and/or dehydrocyclisation and/or isomerisation and/or dehydrogenation reaction. They are particularly useful in a process for the dehydrocyclisation and/or isomerisation of aliphatic hydrocarbons in which the hydrocarbons are contacted at a temperature of from 370° to 600° C., preferably 430° to 550° C., with a catalyst comprising zeolite L of the invention, preferably having at least 90% of the exchangeable cations M as alkali metal ions, and incorporating at least one Group VIII metal having dehydrogenating activity, so as to convert at least part of the aliphatic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbons such as methylcyclopentene may also be used. In a preferred aspect the feed to a process for preparing aromatic hydrocarbons and particularly benzene comprises hexanes. The temperature of the catalytic reaction may be from 370° to 600° C., preferably 430° to 550° C. and preferably pressures in excess of atmospheric are used, for example up to 2000 KPa, more preferably 500 to 1000 KPa. Hydrogen is employed in the formation of aromatic hydrocarbons preferably with a hydrogen to feed ratio of less than 10.

The process is preferably otherwise carried out in the manner described in U.S. Pat. No. 4,104,320, BE 888365, EP 40119, EP 0142351, EP 0145289 or EP0142352.

It has been found that use of the zeolite L of the invention in this way enables greatly improved catalyst lifetimes to be achieved as compared to the lifetime obtained with a conventionally prepared zeolite.

The invention will now be described in more detail, though only by way of illustration, in the following examples and evaluations.

COMPARATIVE EXAMPLE 1

Preparation of Zeolite L

Zeolite L was prepared according to the procedure of EP 0096479. A synthesis gel was prepared having the following composition expressed in moles of pure oxide:

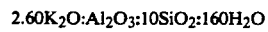

This gel was prepared as follows:

The aluminium hydroxide was dissolved by boiling in an aqueous solution of potassium hydroxide pellets (86% pure KOH) to form Solution A. After dissolution any water loss was corrected. A separate solution, Solution B, was prepared by diluting colloidal silica (Ludox HS 40) with water.

Solutions A and B were mixed for two minutes to form a gel, and just before the gel became fully stiff, it was transferred to a Teflon-lined autoclave, preheated to 150° C. and held at that temperature for 72 hours to bring about crystallisation.

The formed zeolite L was highly crystalline with a typical zeolite L x-ray diffraction (XRD) pattern. Scanning electron micrographs (SEM) show the product to be formed solely of cylindrical crystals having a mean diameter of 1 to 2 microns, an aspect ratio (m/d) of 0.5–1 and an m/h ratio of 0.65–0.85. The $SiO_2:Al_2O_3$ ratio in the product was 6.3.

COMPARATIVE EXAMPLE 2-6

Variation of potassium content

As shown in Table 1, the variation of the amount of potassium in the case where M=K was also investigated. Variation of potassium content from 2.41 moles $K_2O$ (Example 3) to 2.75 moles $K_2O$ (Example 2) gave zeolite L with a cylindrical form, but with m/h<1. Example 4 gave zeolite L with a morphology intermediate a clam shape and the cylinder shape—that is, m/h was very much less than 1.

A low potassium content of 2.15 moles $K_2O$ (Example 5) gave a product with low crystallinity. A high potassium content of 3.4 moles $K_2O$ (Example 6) gave a clam-shaped product.

EXAMPLE 7

Preparation of zeolite L of the invention

The procedure of Example 1 was modified by the addition of certain metal cations to the synthesis gel.

Solution A was prepared from:

| | |
|---|---|
| KOH (87.5% KOH) pellets | 30.81 g |
| Aluminium hydroxide | 15.61 g |
| Water | 49.82 g |
| Additional water | 25.39 g |

The aluminium hydroxide powder was dissolved in the potassium hydroxide solution by boiling. After cooling to ambient temperature, the water loss was corrected.

Solution B was prepared from:

| | |
|---|---|
| Barium hydroxide $Ba(OH)_2.8H_2O$ | 0.17 g |
| Silica (Ludox HS 40) | 150.16 g |
| Water | 120.32 g |
| Seeds of zeolite L from Example 1 | 0.75 g |

Barium hydroxide powder was added to the colloidal silica solution, which gelled on mixing. The synthesis gel was seeded with pre-formed zeolite L crystallites to enhance the crystallization process, but such seeding is not essential.

Solution A was added to Solution B and mixed for 5 minutes to form the synthesis gel. This had the composition (in moles of oxides):

2.4K$_2$O:0.005BaO:Al$_2$O$_3$:10SiO$_2$:164H$_2$O

Crystallisation was conducted at 175° C. for 73 hours. The product was washed 4 times with 500 cm$^3$ water. The pH of the water from the last washing was 10.6. The product was dried at 125° C. and the results are given in Table 3. The barium content of the product was measured to be about 300 ppm by atomic adsorption spectroscopy, and about 80 ppm by ion plasma emmission spectroscopy.

EXAMPLES 8-17

Preparation of zeolite L of the invention

The procedure of Example 7 was repeated with different amounts of barium present and using magnesium and calcium in place of barium, with and without seeding. The synthesis conditions are set out in Table 2 and the details of the products are given in Table 3.

TABLE 1

| Comparative Example | Gel Composition (moles) | | | | Product (wt %) | | | | |
|---|---|---|---|---|---|---|---|---|---|
| | K$_2$O | Al$_2$O$_3$ | SiO$_2$ | H$_2$O | K$_2$O | Al$_2$O$_3$ | SiO$_2$ | H$_2$O | |
| 2 | 2.75 | 1 | 10 | 160 | 6.7 | 2.7 | 15.6 | 75.0 | cylindrical zeolite L (m/h < 1) |
| 3 | 2.41 | 1 | 10 | 160 | 5.9 | 2.7 | 15.8 | 75.6 | cylindrical zeolite L (m/h < 1) |
| 4 | 3.01 | 1 | 10 | 160 | 7.3 | 2.6 | 15.5 | 74.5 | clam/cylinder zeolite L (m/h << 1) |
| 5 | 2.15 | 1 | 10 | 160 | 5.3 | 2.7 | 15.9 | 76.1 | low crystallinity product |
| 6 | 3.4 | 1 | 10 | 160 | 8.2 | 2.6 | 15.4 | 73.8 | clam-shaped zeolite L |

TABLE 2

| Example | Synthesis Gel (moles) | | | | | | Crystallization Conditions | | |
|---|---|---|---|---|---|---|---|---|---|
| | M$^{II}$ | K$_2/n$O | M$^{II}$$_{2}$O | Al$_2$O$_3$ | SiO$_2$ | H$_2$O | Temp (°C.) | Time (hrs) | Gel Seeded |
| 7 | Ba | 2.40 | 0.005 | 1 | 10 | 164 | 175 | 73 | yes |
| 8 | Ba | 2.60 | 0.01 | 1 | 10 | 159 | 175 | 87.5 | yes |
| 9 | Ba | 2.60 | 0.05 | 1 | 10 | 160 | 150 + 175 | 73 + 49 | no |
| 10 | Ba | 2.60 | 0.2 | 1 | 10 | 160 | 150 (+175) | 73 (+24 no change) | yes |
| 11 | Mg | 2.29 | 0.1 | 1 | 10 | 161 | 150 | 68 | yes |
| 12 | Mg | 2.59 | 0.1 | 1 | 10 | 163 | 150 | 65 | yes |
| 13 | Ca | 2.58 | 0.1 | 1 | 10 | 162 | 150 | 65 | yes |
| 14 | Ca | 2.29 | 0.1 | 1 | 10 | 162 | 150 | 135 | yes |
| 15 | Ba | 2.21 | 0.005 | 1 | 10 | 162 | 175 | 65 | no |
| 16 | Ba | 2.10 | 0.005 | 1 | 10 | 161 | 175 | 77 | no |
| 17 | Ba | 2.01 | 0.005 | 1 | 10 | 162 | 175 | 77 | no |

TABLE 3

| Example | Product (moles) | | | | Crystallinity (relative to Ex. 1) % | W/L a) ratio | Zeolite Type | Morphology | Mean Dia(μ) | Aspect Ratio | |
|---|---|---|---|---|---|---|---|---|---|---|---|
| | K$_2$O | M$^{II}$$_{2/n}$O | Al$_2$O$_3$ | SiO$_2$ | | | | | | L/d | L/h |
| 7 | 1.04 | 0.0001 | 1 | 6.7 | 99 | <0.01 | L | cylinder | 0.3–0.5 | 1–3 | 1 |
| 8 | 1.00 | 0.005 | 1 | 6.4 | 81 | <0.01 | L | cylinder | 0.2 | | |
| 9 | not analyzed | | | | 50 | <0.01 | L | | 0.05–0.1 | ? | ? |
| 10 | not analyzed | | | | 40 | <0.01 | L | cylinder | 0.1–0.3 | | |
| 11 | 1.07 | 0.04 | 1 | 6.9 | 92 | <0.01 | L | cylinder | 0.3–0.5 | 1–1.5 | 0.85–1 |
| 12 | 1.11 | 0.04 | 1 | 6.8 | 84 | <0.01 | L | cylinder | 0.2–0.3 | 0.8–1 | ? |
| 13 | 1.08 | 0.05 | 1 | 7.0 | 62 | <0.01 | L | cylinder | 0.2–0.4 | | |
| 14 | alien phase | | | | 0 | <0.01 | no L | plate | — | — | — |
| 15 | 0.90 | 0.004 | 1 | 6.3 | | <0.01 | L | cylinder | 0.2–0.4 | 1–4 | 1 |
| 16 | 0.98 | 0.003 | 1 | 6.7 | 76 | 0.45 | L | cylinder | 0.3–0.5 | 1–4 | 1 |
| 17 | 1.12 | 0.004 | 1 | 8 | | 0.8 | L | cylinder | 0.3–0.6 | 2–6 | 1 |

*"?" indicates that the parameter could not be determined at the resolution of the microscopic analysis used.
a) ratio XRD peak intensity of zeolite W at d = 7.09Å/zeolite L at d = 22.7 Å

The products obtained are in Examples 8 to 13—small cylindrical particles of zeolite L. In Example 14, no zeolite L was seen after 65 hours, and by extending the crystallisation time, an alien phase (unidentified) was produced. Thus, for calcium addition, the gel and crystallisation conditions were inappropriate for zeolite L formation, but Example 13 shows that for that particular additional metal at higher potassium levels, zeolite L is produced. It is necessary to select the crystallisation temperature and time to optimise zeolite L preparation for a given synthesis gel composition, and shorter crystallisation times with the Example 14 gel may increase zeolite L production.

EXAMPLE 18

Stirred zeolite L synthesis

The procedure of Example 8 was repeated except that the crystallisation was carried out for 136 hours at only 100° C. while stirring at 25 rpm. By way of comparison, a synthesis was conducted under the same conditions using gel containing no barium but otherwise identical.

| | BaO/Al$_2$O$_3$ | Crystallization | Zeolite | d(μ) |
|---|---|---|---|---|
| Example 18 | 0.01 | 100° C./136 hours/ 25 rpm | L | 0.1-0.2 |
| Comparison | 0 | 100° C./144 hours; 25 rpm | W | |

Conducting the synthesis of Example 18 without barium and without stirring at 100° C. takes in excess of 400 hours to produce zeolite L.

EXAMPLES 19 to 21

Effect of additional metal on particle size

The procedure of Example 7 was repeated using synthesis 5 gels with a molar composition of:

2.39K$_2$O/xBaO/Al$_2$O$_3$/10SiO$_2$/164H$_2$O in which the Ba content x was varied from 0.01 to 0.04. These were crystallized for 72 hours at 170° C. in 300 ml stainless steel autoclaves. The resulting crystalline products were examined by X-ray diffraction and scanning electron microscopy. The products were pure Zeolite L. As shown in the table below, the crystallite size was gradually reduced with increasing Ba content in the gel:

| | Influence Ba content in gel on KL's crystallite size | |
|---|---|---|
| Example | Ba content (moles/10 moles SiO$_2$) | Crystallite size length * width (microns) |
| 7 | 0.005 | 0.7 * 0.4 |
| 19 | 0.01 | 0.4 * 0.2 |
| 20 | 0.02 | 0.2 * 0.2 |
| 21 | 0.04 | 0.1 * 0.1 |

EXAMPLE 22 and Comparative Example 23

Effect of Alumina Content

The procedure of Example 7 was repeated using synthesis gels with the following compositions:

| Ex 22: | 2.41K$_2$O: 0.005BaO: 1.51Al$_2$O$_3$: 10SiO$_2$: 162H$_2$O |
|---|---|
| Comp Ex 23 | 2.41K$_2$O: 0.005BaO: 1.76Al$_2$O$_3$: 10SiO$_2$: 163H$_2$O | without the addition of seeds. These gels were crystallized for 57 hours at 175° C.

Example 22, which the prior art suggests would result in zeolite W formation because of the high alumina content, gave a 21.4 wt % yield of zeolite L. XRD investigations showed this product to be highly crystalline zeolite L with a low level of zeolite L contamination. W/L ratio (as defined hereinbefore) is measured as 0.09.

Comparative Example 23 gave a pure zeolite W product, indicating that a SiO$_2$/Al$_2$O$_3$ of 5.68 was too low for the alkalinity and water content chosen.

EXAMPLES 24 AND 25

Zeolite L synthesis in the presence of zinc

EXAMPLE 24

A synthesis gel with a molar composition of:

2.31K$_2$O/0.1ZnO/Al$_2$O$_3$/10SiO$_2$/160H$_2$O containing 0.1 wt % preformed KL crystallites as a seed was crystallized at 150° C. for 65 hours in a 300 ml stainless steel autoclave.

XRD showed that the product was an excellent crystalline (82% vs Comparative Example 1) product free of zeolite W and other crystalline contaminants. SEM showed that the product consisted of 0.2 micron cylindrical crystallites with an m/d ratio between 1 and 2.

EXAMPLE 25

In this experiment the Zn content in the gel was, compared with example 1, reduced by 80%, i.e. the gel composition was:

2.31 K$_2$/0.02 ZnO/Al$_2$O$_3$/10 SiO$_2$/161 H$_2$O

This gel was aged at 150° C. for 67.5 hours in a 300 ml stainless steel autoclave. XRD showed that the product again was pure zeolite L without contaminants. The XRD crystallinity of the product was 103% vs comparative Example 1 indicating the presence of larger crystallites. SEM indeed showed that the product consisted of 0.7 micron cylindrical crystallites with an m/d ratio of 1.5. The cylindrical crystallites had a 'perfect' appearance—i.e. very flat basal planes.

This demonstrates that even trace amounts of Zn$^{2+}$ species sufficiently supress the formation of zeolite-W and the crystallite size can be finely tuned by adjusting the Zn content in the synthesis mixture.

EXAMPLE 26

Unseeded synthesis

The procedure of Example 7 was repeated but without the addition of seeds. A substantially similar zeolite L product was obtained with the characteristics and properties set out in Example 7.

EXAMPLE 27

Use of Different Barium Salts

Example 26 was repeated replacing barium hydroxide by a series of insoluble barium salts as the source of barium. The synthesis gel and crystallization conditions were otherwise identical to those used in Example 26. The results are given below:

| Ba Source | Product | W/L Ratio | L/d | L/n |
|---|---|---|---|---|
| Barium Sulphate | Cylindrical zeolite L | <0.01 | >1 | 1 |
| Barium Carbonate | Cylindrical zeolite L | <0.01 | >1 | 1 |
| Barium Silicate | Cylindrical zeolite L | <0.01 | >1 | 1 |

Despite these barium sources being insoluble in water the synthesis is in each case effective in producing the cylindrical crystallites of zeolite L having flat basal planes.

EXAMPLES 28-30 AND COMPARATIVE EXAMPLES 31 AND 32

Replacement of Potassium by Sodium

The procedure of comparative Example 1 was repeated replacing 30% and 40% (molar) of the potassium by sodium in the synthesis gel, by employing sodium hydroxide in place of the appropriate proportion of potassium hydroxide. In each case two syntheses were carried out, one with the addition of barium hydroxide (in an amount of 0.005 moles BaO per mole of $Al_2O_3$) and one without. The synthesis gels were each crystallized for 67.5 hours at 150° C. in a stainless steel autoclave. The results are given below:

| Example | $Na_2O/K_2O + Na_2O$ (molar ratio) | Ba (moles BaO/ mole $Al_2O_3$) | Product | W/L Ratio |
|---|---|---|---|---|
| 28 | 0.3 | 0.005 | Zeolite L 99% crystalline* | 0.02 |
| 29 | 0.4 | 0.005 | Zeolite L 99% crystalline* | 0.02 |
| 30 | 0.5 | 0.005 | Zeolite L | 0.3 |
| Comp. 31 | 0.3 | 0 | Zeolite L | 0.3 |
| Comp. 32 | 0.4 | 0 | ? | 0.5 |

*Crystallinity relative to Comp. Example 1.

The Examples show that in the presence of large amounts of sodium which otherwise tend to lead to zeolite W formation, the introduction of small amounts of barium enhances zeolite L formation.

EXAMPLES 33–36 AND COMPARATIVE EXAMPLES 37–41

Investigation of Differnt Additional Metals

Synthesis gels were prepared by the general procedure of Example 1 with the following gel composition, expressed in terms of moles of oxides:

$$2.35K_2O: Al_2O_3: 10\ SiO_2: 160\ H_2O$$

to which had been added small amounts of various additional metals as set out below. The gels were crystallized for 66 hours at 175° in a 300 ml stainless steel autoclave. The product obtained is also indicated in Table A below.

These results show that the additional metals of the process of the invention give reduced zeolite W formation and smaller crystals of zeolite L than can be obtained in the absence of additional metal or in the presence of Hg, Cd, Fe or La.

EXAMPLES 42–44

Variation of Cobalt Concentration

The procedure of Example 34 was repeated with reduced amounts of added cobalt, introduced as cobalt nitrate hexahydrate. The results obtained are set out in Table B below.

This shows that the size reduction obtained with cobalt (of Comparative Example 41) is even greater than obtained with barium.

EXAMPLES 45–52

Variation in Magnesium Concentration

The procedure of Example 34 was repeated but replacing cobalt with various concentrations of magnesium, added either as magnesium hydroxide or magnesium nitrate. The results obtained are set out in Table C below.

TABLE A

| Example | Additional metal Source | moles/$10SiO_2$ | Product % Crystallinity (vs. Ex. 1) | W/L Ratio | Zeolite L | Cylinder L ($\mu$) | d ($\mu$) |
|---|---|---|---|---|---|---|---|
| 33 | $MnCl_2.4H_2O$ | 0.051 | 84 | 0.01 | Yes | 0.4–0.7 | 0.2–0.5 |
| 34 | $Co(No_3)_2.6H_2O$ | 0.050 | 43* | 0 | Yes | 0.1 | 0.05 |
| 35 | $Ni(No_3)_2.6H^2O$ | 0.025 | 82 | 0 | Yes | 0.2–0.6 | 0.2–0.4 |
| 36 | $Cr(NO_3)_3.9H_2O$ | 0.025 | 98 | 0.02 | Yes | 3–4 | 1.5–2 |
| Comp. 37 | $HgCl_2$ | 0.050 | 76 | 0.23 | Yes | 3–4 | 1.5–2 |
| Comp. 38 | $CdSO_4.8H_2O$ | 0.050 | 81 | 0.49 | Yes | 3–4 | 1.5–2 |
| Comp. 39 | $FeSO_4.7H_2O$ | 0.027 | 93 | 0.10 | Yes | 3–4 | 1.5–2 |
| Comp. 40 | $La(OH)_3$ | 0.026 | 82 | 0.15 | Yes | 3–4 | 1.5–2 |
| Comp. 41 | — | 0 | 98 | 0.10 | Yes | 3–4 | 1.5–2 |

*Apparent low crystallinity as measured by peak height, is caused by peak height reduction resulting from very small crystals rather than amorphous product.

TABLE B

| Example | Co consn. Co/$10SiO_2$ (moles) | in gel (ppm) | Product % crystallinity (vs. Ex. 1)* | W/L Ratio | Cylinders L($\mu$) | d($\mu$) | L/h |
|---|---|---|---|---|---|---|---|
| 42 | 0.0051 | 75 | 70 | 0 | ≦0.2 | ≦0.15 | ~1 |
| 43 | 0.0013 | 20 | 75 | 0 | 0.2–0.3 | 0.1–0.2 | ~1 |
| 44 | 0.0002 | 3 | 90 | 0 | 0.5–0.8 | 0.3–0.5 | ~1 |

*Product crystallinity measured by peak height is apparently lower as a result of small crystals giving reduced peak height. High resolution microscopy indicated no significant amount of amorphous material.

TABLE C

| Example | Mg source | Mg consn. Mg/$10SiO_2$ (moles) | in gel ppm | Product W/L ratio | Cylinders L($\mu$) | d($\mu$) | L/h |
|---|---|---|---|---|---|---|---|
| 45 | $Mg(OH)_2$ | 0.050 | 315 | 0 | 0.5–1 | 0.3–0.5 | ~1 |
| 46 | $Mg(NO_3)_2$ | 0.050 | 315 | 0 | ≦0.2 | ≦0.1 | ~1 |
| 47 | $Mg(NO_3)_2$ | 0.0051 | 35 | 0 | 0.3–0.6 | 0.2–0.3 | ~1 |
| 48 | $Mg(NO_3)_2$ | 0.0026 | 20 | 0 | 0.4–0.7 | 0.3–0.4 | ~1 |
| 49 | $Mg(NO_3)_2$ | | 9 | 0 | 0.5 | 0.1–0.3 | ~1 |
| 50 | $Mg(NO_3)_2$ | | 6 | 0 | 0.7 | 0.2–0.4 | ~1 |

TABLE C-continued

| Example | Mg source | Mg consn. Mg/10SiO$_2$ (moles) | in gel ppm | Product W/L ratio | Cylinders L(μ) | d(μ) | L/h |
|---|---|---|---|---|---|---|---|
| 51 | Mg(NO$_3$)$_2$ | 3 | | 0 | 1 | 0.5–0.6 | ~1 |

These results show the effect of even small amounts of magnesium at promoting the formation of zeolite L, since a similar synthesis without added magnesium (Comparative Example 41) resulted in significant amounts of zeolite W. The results also show the effect of increasing amounts of magnesium in decreasing the size of the formed zeolite L crystallites.

EXAMPLE 52

Effect of magnesium on an aluminium-rich synthesis

The procedure of Comparative Example 1 was repeated to prepare a synthesis gel of the composition

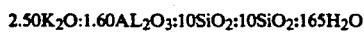

2.50K$_2$O:1.60AL$_2$O$_3$:10SiO$_2$:10SiO$_2$:165H$_2$O to which had been added 15 ppm Mg, as Mg(NO$_3$)$_2$ according to the procedure of Example 11. The gel was crystallized in an autoclave at 125° C. for 23 hours and at 175° C. for a further 66 hours.

The process yielded more than 20% of a zeolite L product with a W/L ratio of 0, thus with no contaminating zeolite W which EP0096479 has shown to be formed at high levels of Al$_2$O$_3$ in the absence of additional metal. The product was in the form of cylindrical crystallites with a length of 0.3–0.5 microns and a diameter of 0.2–0.3 microns.

Evaluation: Aromatisation

The performance of certain of the zeolite L samples of the examples as a catalyst base in aromatisation was compared to products of EP0096479. In each case, a catalyst was prepared by impregnating the base with 0.64 weight % platinum by an incipient wetness technique in which the base was dried at 140° C. overnight then added to a 1.68 wt % solution of platinum tetraamine dichloride monohydrate, stirred and aged at room temperature for 30 minutes, then dried in a vacuum oven at 120° C. for 4 hours. The impregnated sample was dried at 110° C. for 4 hours, and then pelletised, crushed to 16–45 mesh (US seive size) and loaded into a vertical tubular reactor, calcined in air (substantially water-free) at 480° C., and then reduced in hydrogen at 510° C.

An aromatisation screening test was carried out at a temperature of 510° C. and 738 KPa (107 psig) pressure with a C$_6$ mixed feed comprising:

| Component | Weight % |
|---|---|
| iso-C$_6$ (3-methyl-pentane) | 60 |
| n - C$_6$ | 40 | at a weight hourly space velocity of 8.0 w/w hr$^{-1}$ and in the presence of hydrogen, the H$_2$:hydrocarbon ratio being 4. This is an accelerated test which provides a good correlation with catalyst performance in commercial aromatisation. The results are given in Table 4.

A catalyst using the zeolite of Example 7 as its catalyst base is compared with a catalyst using a zeolite L prepared according to EP0096479 with cylindrical particles (d=0.7–1.4μ, m/d=0.5–1, m/h=0.67), an SiO$_2$./Al$_2$O$_3$ ratio of 5.8 and containing no additional metal M$^{11}$, hereinafter referred to as "Comparison"

TABLE 4

| | Example 7 Time On Stream (hr) | | Comparison Time On Stream (hr) | |
|---|---|---|---|---|
| | 22 | 50 | 22 | 50 |
| C$_6$ Conversion (%) | 81.6 | 77.2 | 74.9 | 68.4 |
| Benzene Yield (%) | 60.2 | 57.7 | 51.5 | 46.6 |
| Benzene Selectivity (%) | 73.8 | 74.8 | 68.7 | 68.1 |

A 16% (relative) higher benzene yield was observed with the invention whereas no changes in C$_4$-cracking pattern were observed. The higher aromatics yield is to improved activity (conversion) and to improved selectivity.

Further aromatisation screening test were carried out on catalysts prepared using the following materials as substrate.

(a) zeolite L of Example 26;
(b) zeolite L of Example 26, exchanged with an aqueous 1N potassium nitrate solution for 24 hours at ambient temperature and then dried at 120° C. for four hours prior to impregnation with platinum as described above-the Ba content is reduced to 50 ppm (as measured by ion plasma emission spectroscopy);
(c) Comparison, as defined above;
(d) Comparison, exchanged with barium as described in Example 1 of GB 2116450 to give a Ba content of 100 ppm as measured by ion plasma emmission spectroscopy, prior to impregnation with platinum as described above.

TABLE 5

| | Example 7 Scale-up | Example 7 -K exchanged | Comparison | Comparison Ba exchanged |
|---|---|---|---|---|
| | Time on stream (hr) | | | |
| | 23 | 23 | 23 | 23 |
| C$_6$ Conversion (%) | 78.7 | 76.3 | 74.9 | 70.1 |
| Benzene yield (%) | 58.2 | 56.9 | 51.2 | 48.8 |
| Benzene selectivity (%) | 74.0 | 74.6 | 68.4 | 69.6 |

These results shown that the zeolite L of the invention is better in terms of conversion, yield and selectivity than the zeolite L described in EP 0096749, in this catalytic application. Exchanging the zeolite L of the invention did not remove all barium from the sample, showing that the barium is not all in an exchangeable form, but by removing the exchangeable barium the advantage over the zeolite L of EP 0096479 is not lost. Furthermore, carrying out the barium exchange procedure of GB 2116450 on the zeolite L of EP 0096479 did not improve the performance of the zeolite L in the terms of conversion or benzene yield, but rather made it worse, and the change in benzene selectivity is relatively small. This comparison shows that the advantage of the zeolite L of the invention does not lie in barium exchange as described in GB 2116450.

I claim:

1. A process for the preparation of zeolite L crystallites in the form of cylinders, containing reduced amounts of zeolite W, in which an alkaline reaction mixture comprising water, a source of alkali metal, a source of silicon and a source of aluminum is heated to a temperature of from at least 75° C. to form the zeolite L, characterized in that the reaction mixture comprises a source of an additional metal $M^{11}$ present such that the amount of $M^{11}$ ranges from about 0.1 ppm to about 0.1 wt % based on said reaction mixture and has a composition falling within the following molar ratios expressed as oxides:

| | |
|---|---|
| $(M^1_2O + M^{11}_{2/n}O)/SiO_2$ | 0.18–0.36 |
| $H_2O/(M^1_2O + M^{11}_{2/n}O)$ | 25–90 |
| $SiO_2/Al_2O_3$ | 5–15 |
| $M^1_2O/(M^1_2O + M^{11}_{2/n}O)$ | 0.900–0.9999 | wherein $M^1$ is potassium or a mixture of potassium and sodium, $M^{11}$ is a cation of magnesium, calcium, barium, manganese, chromium, cobalt, nickel or zinc, and n is the valence of $M^{11}$.

2. A process as claimed in claim 1, in which the reaction mixture is heated to from 100° C. to 250° C.

3. A process as claimed in claim 2, in which the reaction mixture is heated to from 120° C. to 225° C.

4. A process for the preparation of zeolite L, wherein a reaction mixture comprising water, a source of alkali metal consisting of potassium, a source of silicon, and a source of aluminum is heated to a temperature of at least 75° C. to form zeolite L, characterized in that the reaction mixture contains an additional metal $M^{11}$, and that the reaction mixture is such that in the absence of the additional metal $M^{11}$ the final product would comprise substantial amounts of zeolite W, the amount of the additional metal $M^{11}$ being in the range of from about 0.1 ppm to about 0.1 wt% based on the weight of said reaction mixture, wherein $M^{11}$ is a cation of magnesium, calcium, barium, manganese, chromium, cobalt, nickel, or zinc.

5. A process as claimed in claim 1, wherein the reaction mixture comprises:

| | |
|---|---|
| $(M^1_2O + M^{11}_{2/n}O)/SiO_2$ | 0.18–0.26 |
| $H_2O/(M^1_2O + M^{11}_{2/n}O)$ | 50–90 |
| $SiO_2/Al_2O_3$ | 6–12 |
| $M^1_2O/(M^1_2O + M^{11}_{2/n}O)$ | 0.950–0.9999 | where $M^1$ is potassium or a mixture of potassium and a second alkali metal $M^2$ when the molar ratio $K_2O/K_2O+M^2_2O$ is from 0.5 to 1, wherein $M^{11}$ is a cation of magnesium, calcium, barium, manganese, chromium, cobalt, nickel, or zinc and n is the valence of $M^{11}$.

6. A method of suppressing zeolite W formation during the preparation of zeolite L having crystallites of reduced crystallite size from a crystallization gel containing a source of alkali metal which is potassium or a mixture of potassium and sodium, in which the crystallization conditions would otherwise allow zeolite W formation, which method comprises introducing into the gel an amount of a zeolite W-suppressing source of an additional metal $M^{11}$, wherein $M^{11}$ is a cation of magnesium, calcium, barium, manganese, chromium, cobalt, nickel, or zinc, said metal cation present in said gel in an amount of from about 0.1 ppm to about 0.1 wt % based on the weight of said gel.

7. The method of claim 6 wherein the amount of additional metal $M^{11}$ is from 5 ppm to 0.05 wt % based on the weight of the gel.

8. A zeolite L composition comprising cylindrical crystallites having basal planes shaped such that the ratio of axial length of curved cylindrical surface (m) to the overall axial length of the crystallite (h) is greater than 0.9, and the aspect ratio of (m) to the mean diameter (d) is at least 0.5, wherein at least 80% of the basal planes are microscopically flat to within about 200Å and do not exhibit spiral step growths thereon, said zeolite further characterized in that it is crystallized from a synthesis mixture containing a source of alkali metal which is potassium or a mixture of potassium and sodium and also containing a source of additional metal selected from the group consisting of magnesium, calcium, barium, manganese, chromium, cobalt, nickel and zinc cations, said additional metal present in an amount of from about 0.1 ppm to about 0.1 wt % based on said synthesis mixture.

9. The zeolite L composition of claim 8, wherein the cylindrical crystallites have a mean diameter (d) of at least 0.05μ.

10. The zeolite L composition of claim 8, wherein the cylindrical crystallites have a mean diameter (d) of at least 0.1μ.

11. The zeolite L composition of claim 8, wherein the cylindrical crystallites have an aspect ratio of at least 1.

12. The zeolite L composition of claim 8, wherein at least 90% of said basal planes are microscopically flat.

13. The zeolite composition of claim 12 wherein said ratio of (m) to (h) is substantially unity.

14. The method of claim 7 wherein said zeolite L comprises cylindrical crystallites having an aspect ratio of axial length of curved cylinder surface (m) to mean diameter of at least 0.5 and basal planes shaped such that the ratio of (m) to the overall axial length of the crystallite (h) is greater than 0.9 and at least 80% of said basal planes are microscopically flat to within about 200Å and do not exhibit spiral step growths therein.

15. The method of claim 1 wherein said cylindrical crystallites are right cylinders having a mean diameter in the range of from 0.1 to 0.5 microns.

16. The method of claim 1 wherein the ratio of $SiO_2$ to $Al_2O_3$ is in the range of from 5 to 7.5.

17. The method of claim 16 wherein the ratio of $SiO_2$ to $Al_2O_3$ is in the range of from 6.5 to 7.5.

18. The method of claim 1 wherein said cylinders have an aspect ratio of (m) to the mean diameter (d) in the range of from 0.75 to 5.

19. The method of claim 18 wherein said cylindrical crystallites are right cylinders having a mean diameter in the range of from 0.1 to 0.5 microns.

20. The zeolite L composition of claim 8 wherein said cylindrical crystallites are right cylinders having a mean diameter in the range of from 0.1 to 0.5 microns.

21. The zeolite L composition of claim 20 wherein said aspect ratio is in the range of from 0.75 to 5.

22. The zeolite L composition of claim 8 wherein the ratio of $SiO_2$ to $Al_2O_3$ is in the range of from 5 to 7.5.

23. The zeolite L composition of claim 22 wherein the ratio of $SiO_2$ to $Al_2O_3$ is in the range of from 6.5 to 7.5.

24. The zeolite L composition of claim 8 wherein said additional metal is present in an amount of from 5 ppm to 0.05 wt % based on the weight of said synthesis mixture.

25. The zeolite L composition of claim 8 wherein said alkali metal consists of potassium.

26. The zeolite L composition of claim 8 wherein said additional metal cation is barium.

27. The zeolite L composition of claim 8 wherein said additional metal cation is magnesium.

28. The zeolite L composition of claim 8 wherein said additional metal cation is zinc.

* * * * *